United States Patent
Paget et al.

(10) Patent No.: US 9,988,326 B2
(45) Date of Patent: Jun. 5, 2018

(54) METHOD FOR THE FINAL PURIFICATION OF BIOGAS FOR PRODUCING BIOMETHANE

(71) Applicant: L'Air Liquide, Societe Anonyme pour l'Etude et l'Exploitation des Procedes Georges Claude, Paris (FR)

(72) Inventors: Nicolas Paget, Saint Martin d'Heres (FR); Guenael Prince, Saint Egreve (FR); Golo Zick, Fontaine (FR)

(73) Assignee: L'AIR LIQUIDE SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 265 days.

(21) Appl. No.: 15/022,309

(22) PCT Filed: Sep. 11, 2014

(86) PCT No.: PCT/FR2014/052259
§ 371 (c)(1),
(2) Date: Mar. 16, 2016

(87) PCT Pub. No.: WO2015/036709
PCT Pub. Date: Mar. 19, 2015

(65) Prior Publication Data
US 2016/0229771 A1  Aug. 11, 2016

(30) Foreign Application Priority Data
Sep. 16, 2013 (FR) ..................... 13 58901

(51) Int. Cl.
*C07C 7/144* (2006.01)
*B01D 53/22* (2006.01)

(52) U.S. Cl.
CPC ............ *C07C 7/144* (2013.01); *B01D 53/226* (2013.01); *B01D 2256/22* (2013.01);
(Continued)

(58) Field of Classification Search
CPC .. C07C 7/144; B01D 53/226; B01D 2256/22; B01D 2256/245; B01D 2257/80;
(Continued)

(56) References Cited

U.S. PATENT DOCUMENTS 6,565,626 B1  5/2003  Baker et al.
6,630,011 B1  10/2003  Baker et al.
(Continued)

FOREIGN PATENT DOCUMENTS

DE  102004007548  9/2005
WO  WO-2012000727 A1 *  1/2012  ........... B01D 53/226

OTHER PUBLICATIONS

International Search Report and Written Opinion for PCT/FR2014/052259, dated Nov. 27, 2014.
French Search Report for FR1358901, dated Jun. 10, 2014.

*Primary Examiner* — Brian A McCaig
*Assistant Examiner* — Jason Y Chong
(74) *Attorney, Agent, or Firm* — Christopher J. Cronin

(57) ABSTRACT

A four-stage membrane separation unit purification process, especially for prepurified biogas, in which a retentate from the first stage is fed as feed gas to a second stage, a permeate from the first stage is fed as feed gas to a third stage, a retentate from the third stage is fed as feed gas to a fourth stage.

11 Claims, 2 Drawing Sheets

(52) U.S. Cl.
CPC .. *B01D 2256/245* (2013.01); *B01D 2257/504* (2013.01); *B01D 2257/708* (2013.01); *B01D 2257/80* (2013.01); *B01D 2258/05* (2013.01); *Y02C 10/10* (2013.01)

(58) Field of Classification Search
CPC ........ B01D 2257/504; B01D 2257/708; B01D 2258/05; Y02C 10/10
See application file for complete search history.

(56) References Cited

U.S. PATENT DOCUMENTS

| | | |
|---|---|---|
| 2004/0099138 A1 | 5/2004 | Karode et al. |
| 2007/0125537 A1 | 6/2007 | Lokhandwala et al. |
| 2013/0098242 A1 | 4/2013 | Ungerank et al. |

\* cited by examiner

METHOD FOR THE FINAL PURIFICATION OF BIOGAS FOR PRODUCING BIOMETHANE

CROSS-REFERENCE TO RELATED APPLICATIONS

This application is a § 371 of International PCT Application PCT/FR2014/052259, filed Sep. 11, 2014, which claims § 119(a) foreign priority to French patent application FR1358901, filed Sep. 16, 2013.

BACKGROUND

Field of the Invention

The present invention relates to a membrane permeation process for treating a gas stream containing at least methane and carbon dioxide in order to produce a methane-rich gas stream—the methane content of which is in accordance with the requirements for the use thereof.

In particular, it relates to biogas purification, with the objective of producing biomethane in accordance with the specifications for injection into a natural gas network.

Related Art

Biogas is the gas produced during the degradation of organic matter in the absence of oxygen (anaerobic fermentation), also referred to as methanization. This may be a natural degradation—it is thus observed in marshes or municipal waste landfill sites—but the production of biogas may also result from the methanization of waste in a dedicated reactor, referred to as a methanizer or digester.

Due to its main constituents—methane and carbon dioxide—biogas is a potent greenhouse gas; at the same time it is also a significant renewable energy source in the context of the increasing scarcity of fossil fuels.

Biogas predominantly contains methane ($CH_4$) and carbon dioxide ($CO_2$) in proportions that vary as a function of the production method, but also, in smaller proportions, water, nitrogen, hydrogen sulfide, oxygen, and also other organic compounds, in trace amounts.

Depending on the organic matter degraded and the techniques used, the proportions of the components differ, but on average biogas comprises, as dry gas, from 30% to 75% methane, from 15% to 60% $CO_2$, from 0 to 15% nitrogen, from 0 to 5% oxygen and trace compounds.

Biogas is upgraded in various ways. It may, after slight treatment, be upgraded in the vicinity of the production site in order to provide heat, electricity or a mixture of both (cogeneration); the high content of carbon dioxide reduces its heating value, increases the compression and transport costs and limits the economic advantages of upgrading it to this local use.

A more thorough purification of the biogas enables a broader use thereof, in particular a thorough purification of the biogas makes it possible to obtain a biogas that is purified to the specifications of natural gas and which could be substituted therefor. Biogas thus purified is "biomethane". Biomethane thus supplements natural gas resources with a renewable portion produced at the heart of territories; it can be used for exactly the same uses as natural gas of fossil origin. It may supply a natural gas network or a vehicle filling station and it may also be liquefied in order to be stored in the form of liquefied natural gas (LNG), etc.

The methods of upgrading biomethane are determined as a function of local contexts: local energy requirements, possibilities of upgrading as biomethane fuel, existence nearby of networks for distributing or transporting natural gas in particular. Creating synergies between the various operators working in a territory (farmers, manufacturers, public authorities), the production of biomethane helps territories to acquire greater energy self-sufficiency.

Several steps must be passed through between collecting the biogas and obtaining biomethane, the final product capable of being compressed or liquefied.

In particular, several steps are necessary before the treatment that aims to separate the carbon dioxide in order to produce a purified methane stream. A first step consists in compressing the biogas that has been produced and transported at atmospheric pressure; this compression may be obtained—conventionally—via a lubricated screw compressor. The next steps aim to strip the biogas of the corrosive components that are hydrogen sulfide and the volatile organic compounds (VOCs); the technologies used are conventionally pressure swing adsorption (PSA) and capture on activated carbon. Next comes the step that consists in separating the carbon dioxide in order to finally provide methane having the purity required for the subsequent use thereof.

Carbon dioxide is a contaminant typically present in natural gas, from which it is common to have to strip it. Various technologies are used for this depending on the situation; among these, membrane technology is particularly effective when the $CO_2$ content is high; it is therefore particularly effective for separating the $CO_2$ present in biogas, and in particular in landfill gas.

The membrane gas separation processes used for the purification of a gas, whether they use one or more membrane stages, must enable the production of a gas having the required quality, for a low cost, while minimizing the losses of the gas that it is desired to upgrade. Thus, in the case of the purification of biogas, the separation carried out is mainly a $CH_4/CO_2$ separation, that must enable the production of a gas containing, depending on the use thereof, more than 85% $CH_4$, preferably more than 95% CH4, more preferably more than 97.5% $CH_4$, while minimizing the losses of $CH_4$ in the waste gas and the purification cost, the latter being for a large part linked to the electricity consumption of the device for compressing the gas upstream of the membranes.

One of the conventional means for improving the recovery of the $CH_4$ in a membrane system is to increase the recycle rate of the waste—an operation that consists in recycling a greater or lesser fraction of the waste to the intake of the compressor. This recycling is offset by an increase in the electricity consumption of the compressor, since the flow to be compressed is larger.

In order to reduce the negative impact of this recycling on the electricity consumption of the compressor, one known solution consists in changing from a one-stage membrane system to a two-stage system in which the waste from the $1^{st}$ stage supplies the $2^{nd}$ stage, and of which only the permeate from the second stage is recycled, the permeate from the $1^{st}$ stage for its part being removed from the process (in general discharged to the atmosphere while optionally passing through an oxidizer in order to oxidize therein the residual methane).

The solution is also known that consists in using a three-stage membrane system, in which the permeate from the $1^{st}$ stage undergoes a second separation in the third membrane stage, before being mixed with the permeate from the $2^{nd}$ stage, in order to be recycled. This three-stage system is used without recompression of the permeate from the $1^{st}$ stage, the permeate from the $2^{nd}$ stage and the waste from the $3^{rd}$ stage are recycled to the inlet of the membrane system. This system with three membrane stages improves the methane yield relative to a system with two membrane stages.

However, although the system with three membrane stages makes it possible to significantly improve the recovery rate of the gas to be upgraded ($CH_4$ in the case of biogas) without adding the cost of an intermediate compressor, it follows that without intermediate compression of the permeate, a good separation is not obtained in the $3^{rd}$ membrane stage, and thus the retentate from the $3^{rd}$ membrane stage contains an even greater proportion of gas to be eliminated which has not permeated in the $3^{rd}$ stage. This gas to be eliminated, which is needlessly recompressed, increases the electricity consumption of the compressor. Thus, in the case of biogas, in the absence of intermediate compression of the permeate from the first membrane before it passes into the third membrane stage, the retentate from the $3^{rd}$ membrane stage will recycle a proportion of $CO_2$ to the inlet of the compressor. It would therefore be advantageous to reduce this proportion of recycled $CO_2$.

Therefore, there remains a need to improve the process for the membrane separation of methane and carbon dioxide contained in a biogas that makes it possible to obtain higher purity methane, with a very good yield, while reducing the operating cost of the system.

SUMMARY OF THE INVENTION

The present invention thus describes a membrane separation process and facility that carry out the membrane separation of the methane and carbon dioxide contained in the biogas, which judiciously uses an arrangement with four membrane stages; an arrangement of four membrane stages according to the invention significantly reduces the cost of compressing the gas relative to the arrangement with three membrane stages according to the prior art while surprisingly retaining a very good yield of methane. A membrane or membrane stage should be understood to mean a single membrane or a bundle of membranes or a module composed of several bundles or of several modules as long as they are parallel with respect to one another.

The invention proposes a membrane permeation process for treating a gas stream containing at least methane and carbon dioxide in order to produce a methane-rich gas stream, comprising at least the following steps:

a step (a) of providing a first membrane separation unit equipped with a first membrane capable of receiving a first feed gas and of supplying a first permeate and a first retentate, said first membrane being more permeable to carbon dioxide than to methane, a step (b) of providing a second membrane separation unit equipped with a second membrane capable of receiving a second feed gas and of supplying a second permeate and a second retentate, said second membrane being more permeable to carbon dioxide than to methane, and said second membrane separation unit being connected in series with the first membrane separation unit so that the first retentate constitutes the second feed gas, a step (c) of providing a third membrane separation unit equipped with a third membrane capable of receiving a third feed gas and of supplying a third permeate and a third retentate, said third membrane being more permeable to carbon dioxide than to methane, and said third membrane separation unit being connected in series with the first membrane separation unit so that the first permeate constitutes the third feed gas, a step (d) of compressing said gas stream containing at least methane and carbon dioxide to be treated in a compressor to a first pressure P1, a step (e) of supplying the first membrane separation unit with the gas stream to be treated at the first pressure P1 so as to produce a retentate that is enriched in methane relative to the gas to be treated and a permeate that is enriched in carbon dioxide relative to the gas to be treated, a step (f) of supplying the second membrane separation unit with the first retentate—enriched in methane relative to the gas stream to be treated—so as to produce a second retentate that is enriched in methane relative to the first retentate and a second permeate that is enriched in carbon dioxide relative to the first retentate, a step (g) of supplying the third membrane separation unit with the first permeate so as to produce a third retentate that is enriched in methane relative to the first permeate and a third permeate that is enriched in carbon dioxide relative to the first permeate and is provided, a step (h) of recycling the second permeate to the compressor of step (d), characterized in that the process additionally comprises:

a step (i) of providing a fourth membrane separation unit equipped with a fourth membrane capable of receiving a feed gas and of supplying a permeate and a retentate, said fourth membrane being more permeable to carbon dioxide than to methane, and said fourth membrane separation unit being connected in series with the third membrane separation unit so that the third retentate constitutes the fourth feed gas, a step (j) of supplying the fourth membrane separation unit with the third retentate so as to produce a fourth retentate that is richer in methane than the third retentate and a fourth permeate that is enriched in carbon dioxide relative to the third retentate, a step (k) of recycling the fourth retentate to the compressor of step (d), a step (l) of providing the fourth permeate.

The third and fourth permeates are discharged from the process; they may—independently or together—be for example treated by thermal oxidation, used for upgrading $CO_2$, or simply released to the atmosphere.

The membrane separation process according to the invention advantageously has all or some of the features below, alone or in combination:

the membranes used may have the same selectivity or at least one membrane separation unit may use a membrane of different selectivity, the gas to be treated may be pre-purified biogas, it being possible for this prepurification, depending on the requirements, to comprise all or some of the following steps: drying, $CO_2$ abatement and elimination of volatile organic compounds (VOCs).

According to another aspect of the invention, this invention relates to a facility for the membrane permeation treatment of a gas stream containing at least methane and carbon dioxide in order to produce a methane-rich gas stream, comprising at least:

a first membrane separation unit equipped with a first membrane capable of receiving a first feed gas and of supplying a first permeate and a first retentate, said first membrane being more permeable to carbon dioxide than to methane, a second membrane separation unit equipped with a second membrane capable of receiving a second feed gas and of supplying a second permeate and a second retentate, said second membrane being more permeable to carbon dioxide than to methane, and said second membrane separation unit being connected in series with the first membrane separation unit so that the first retentate constitutes the second feed gas, a third membrane separation unit equipped with a third membrane capable of receiving a third feed gas and of supplying a third permeate and a third retentate, said third membrane being more permeable to carbon dioxide than to methane, and said third membrane separation unit being connected in series with the first membrane separation unit so that the first permeate constitutes the third feed gas, a compressor C capable of compressing the second permeate to a first pressure P1, a means of supplying the first membrane separation unit with the gas stream to be treated at the first pressure P1, a means of supplying the second membrane separation unit with the first retentate, a means of supplying the third membrane separation unit with the first permeate, a means of recycling the second permeate to the compressor C, characterized in that the facility additionally comprises:

a fourth membrane separation unit that is more permeable to carbon dioxide than to methane, a means of supplying the fourth membrane separation unit with the third retentate, a means of recycling the fourth retentate to the compressor C, a means of providing the fourth permeate.

The facility additionally comprises all or some of the features below, alone or in combination:

the membranes used have the same selectivity, at least one membrane separation unit uses a membrane of different selectivity, the facility comprises means of pre-purifying the biogas to be treated that are capable of carrying out, depending on the requirements, all or some of the functions of drying, $CO_2$ abatement and elimination of volatile organic compounds (VOCs).

The invention will be better understood with the aid of the following description, given with reference to the appended figures.

DETAILED DESCRIPTION OF THE INVENTION

The table below gives the comparative performances of separation processes having two or three membrane stages according to the prior art with the four-membrane process according to the invention, and also, by way of comparison, a process that proposes an additional membrane stage, i.e. a fifth membrane stage in series relative to the fourth stage according to the invention.

TABLE

| Number of stages | $CH_4$ yield | Recycle rate | Specific cost |
| --- | --- | --- | --- |
| 2 | 97.82 | 1.78 | 0.245 |
| 3 | 99.53% | 1.47 | 0.234 |
| 4 | 99.09% | 1.42 | 0.225 |
| 5 | 98.97% | 1.41 | 0.224 |

The first column of the table indicates the number of membranes used.

It is thus observed that the addition of a fourth membrane stage makes it possible to significantly reduce the specific cost.

The addition of the fourth membrane stage in series to the retentate of the $3^{rd}$ stage makes it possible to reduce even further the content of $CO_2$ in the recycle stream, and consequently to reduce the flow to be recompressed. The compromise between the specific cost (electrical power for compression) and the recovery rate of the $CH_4$ is thus optimized.

It is also seen that this advantage is specific to the fourth stage, and that the addition of a fifth stage provides no significant improvement to the process, both in terms of yield and in terms of specific cost.

The figures are described below in detail; the components common to various figures bear the same references in each of the figures where they appear.

Figure 1:
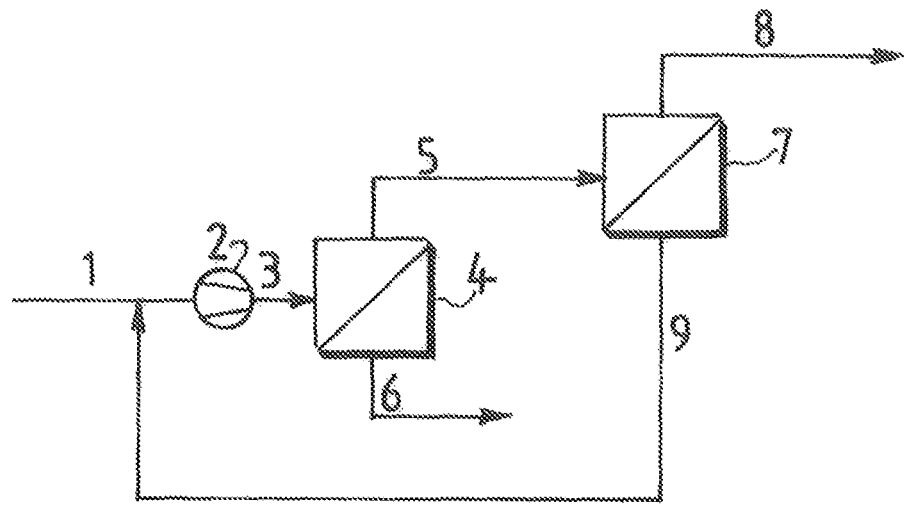
FIG. 1 presents a schematic diagram illustrating the process with two membrane stages according to the prior art.

According to the known prior art process from FIG. 1—having two membrane stages—the biogas to be purified 1 is compressed by the compressor 2; the compressed biogas 3 at a pressure P1 supplies the first membrane stage 4. This first membrane stage consists of membranes that are more permeable to carbon dioxide than to methane. Recovered at the outlet of this first membrane stage are a first retentate 5 at a pressure close to P1, and a first permeate 6.

The first retentate 5 is sent to the feed of a second membrane stage 7 consisting of membranes that are more permeable to carbon dioxide than to methane. Recovered at the outlet of this second membrane stage are a second retentate 8 that is under pressure and rich in methane and a second permeate 9 which is sent back to the compressor 2 in order to be recompressed before being recycled to the feed of the first membrane stage. The first permeate 6 is in the form of a gas stream which is removed from the process in order to be used or released.

Figure 2:
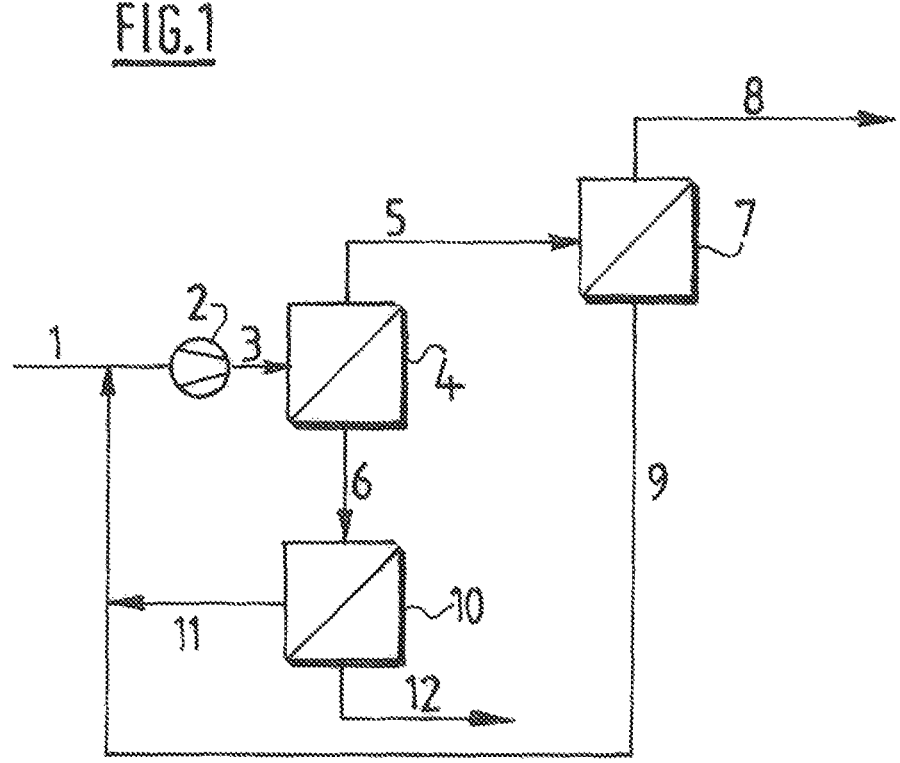
FIG. 2 presents a schematic diagram illustrating the process with three membrane stages according to the prior art.

According to the known prior art process from FIG. 2—having three membrane stages—the biogas to be purified 1 is compressed by the compressor 2; the compressed biogas 3 at a pressure P1 supplies the first membrane stage referenced 4. This first membrane stage consists of membranes that are more permeable to carbon dioxide than to methane. Recovered at the outlet of this first membrane stage are a first retentate 5 at a pressure close to P1, and a first permeate 6.

The first retentate 5 is sent to the feed of a second membrane stage 7 consisting of membranes that are more permeable to carbon dioxide than to methane. Recovered at the outlet of this second membrane stage are a second retentate 8 that is under pressure and rich in methane and a second permeate 9 which is sent back to the compressor 2 in order to be recompressed before being recycled to the feed of the first membrane stage. The first permeate 6 is in the form of a gas stream; it supplies—without intermediate compression—a third membrane stage referenced 10, itself also consisting of membranes that are more permeable to carbon dioxide than to methane. Recovered at the outlet of this third membrane stage are a third retentate 11 that is enriched in methane relative to the first permeate 6 and a third permeate 12. The third permeate 12 is removed from the process in order to be used or released and the third retentate 11 is sent back to the compressor together with the second permeate 9 in order to be recompressed before supplying the first membrane stage. The third permeate 12 is in the form of a gas stream; it is discharged from the process in order to be used or released.

Figure 3:
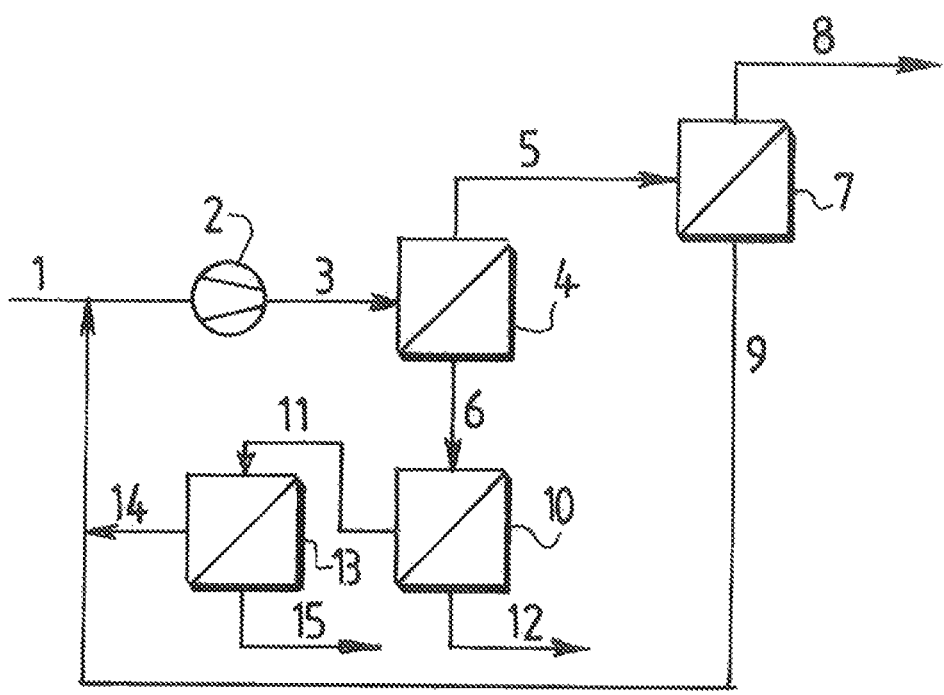
FIG. 3 presents a schematic diagram illustrating the process with four stages according to the invention.

According to the process according to the invention from FIG. 3, a fourth membrane stage is added to the retentate of the third stage. The process of the invention operates in the following manner: the biogas to be purified 1 is compressed by the compressor 2; the compressed biogas 3 at a pressure P1 supplies the first membrane stage referenced 4. This first membrane stage consists of membranes that are more permeable to carbon dioxide than to methane. Recovered at the outlet of this first membrane stage are a first retentate 5 at a pressure close to P1, and a first permeate 6.

The first retentate 5 is sent to the feed of a second membrane stage 7 consisting of membranes that are more permeable to carbon dioxide than to methane. Recovered at the outlet of this second membrane stage are a second retentate 8 that is under pressure and rich in methane and a second permeate 9 which is sent back to the compressor 2 in order to be recompressed before being recycled to the feed of the first membrane stage. The first permeate 6 is in the form of a gas stream; it supplies—without intermediate compression—a third membrane stage referenced 10, itself also consisting of membranes that are more permeable to carbon dioxide than to methane. Recovered at the outlet of this third membrane stage are a third retentate 11 that is enriched in methane relative to the first permeate 6 and a third permeate 12. The third permeate 12 is discharged from the process in order to be used or released and the third retentate 11 supplies—without intermediate compression—a fourth membrane stage referenced 13, itself also consisting of membranes that are more permeable to carbon dioxide than to methane. Recovered at the outlet of this fourth membrane stage are a fourth retentate 14 that is enriched in methane relative to the third retentate 11 and a fourth permeate 15. The fourth permeate 15 is discharged from the process in order to be used or released and the fourth retentate 14 is sent back to the compressor 2 together with the second permeate 9 in order to be recompressed before supplying the first membrane stage.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A membrane permeation process for treating a gas stream containing at least methane and carbon dioxide in order to produce a methane-rich gas stream using a facility comprising a compressor and first, second, third and fourth membrane separation units equipped with first, second, third and fourth membranes, respectively, that are more permeable to carbon dioxide than methane, said method comprising the steps of:
   compressing said gas stream with a compressor to a first pressure;
   supplying a feed gas stream at said first pressure to the first membrane separation unit so as to produce a first retentate that is enriched in methane relative to the compressed gas stream and a first permeate that is enriched in carbon dioxide relative to the compressed gas stream;
   supplying the second membrane separation unit with the first retentate so as to produce a second retentate that is enriched in methane relative to the first retentate and a second permeate that is enriched in carbon dioxide relative to the first retentate;
   supplying the third membrane separation unit with the first permeate so as to produce a third retentate that is enriched in methane relative to the first permeate and a third permeate that is enriched in carbon dioxide relative to the first permeate;
   recycling the second permeate to the compressor;
   supplying the fourth membrane separation unit with the third retentate so as to produce a fourth retentate that is richer in methane than the third retentate and a fourth permeate that is enriched in carbon dioxide relative to the third retentate; and
   recycling the fourth retentate to the compressor, wherein said feed gas stream comprises the compressed gas stream, second permeate, and fourth retentate.

2. The process of claim 1, wherein each of the membranes has a same selectivity.

3. The process of claim 1, wherein at least one of the membranes has selectivity different from other of the membranes.

4. The process of claim 1, wherein the second retentate is methane rich gas.

5. The process of claim 1, wherein the third and fourth permeates are either vented to atmosphere or treated in a thermal oxidizer.

6. The process of claim 1, wherein the gas stream is pre-purified biogas.

7. The process of claim 6, wherein the prepurification includes removal of moisture, $CO_2$, and volatile organic compounds.

8. A facility for membrane permeation treatment of a gas stream containing at least methane and carbon dioxide in order to produce a methane-rich gas stream, comprising:
- a first membrane separation unit equipped with a first membrane configured to receive a feed gas stream and to separate said feed gas stream into a first permeate and a first retentate, said first membrane being more permeable to carbon dioxide than to methane;
- a second membrane separation unit equipped with a second membrane configured to receive said first retentate and to separate said first retentate into a second permeate and a second retentate, said second membrane being more permeable to carbon dioxide than to methane;
- a third membrane separation unit equipped with a third membrane configured to receive said first permeate and to separate said first permeate into a third permeate and a third retentate, said third membrane being more permeable to carbon dioxide than to methane;
- a fourth membrane separation unit equipped with a fourth membrane configured to receive said third retentate and to separate said third retentate into a fourth permeate and a fourth retentate; and
- a compressor configured to receive said gas stream, second permeate, and fourth retentate and to compress said gas stream, second permeate, and fourth retentate to a first pressure to obtain said feed gas stream wherein said feed gas comprises said compressed gas stream, second permeate, and fourth retentate and is supplied to the first membrane separation unit.

9. The facility of claim 8, wherein each of the membranes has a same selectivity.

10. The facility of claim 8, wherein at least one of said membranes has a selectivity that is different than other of said membranes.

11. The facility of claim 8, further comprising a thermal oxidizer configured to receive the third and fourth permeates.

* * * * *